United States Patent [19]

Martin

[11] Patent Number: 4,551,243

[45] Date of Patent: Nov. 5, 1985

[54] ANAEROBIC DIGESTER

[75] Inventor: John H. Martin, Gosport, Ind.

[73] Assignee: Energy Cycle, Inc., Kansas City, Mo.

[21] Appl. No.: 408,073

[22] Filed: Aug. 16, 1982

[51] Int. Cl.$^4$ .............................................. B01D 35/18
[52] U.S. Cl. ................................. 210/180; 210/523; 210/539; 71/9; 71/10
[58] Field of Search ........................................ 71/8–10; 210/180, 523, 539; 435/313, 316, 801, 802

[56] References Cited

U.S. PATENT DOCUMENTS

| | | | |
|---|---|---|---|
| 4,100,023 | 7/1978 | McDonald | 71/10 X |
| 4,274,838 | 6/1981 | Dale et al. | 210/180 X |

Primary Examiner—Ferris H. Lander
Attorney, Agent, or Firm—Vincent L. Carney

[57] ABSTRACT

To reduce the accumulation of undesirable solid material within an anaerobic digester, new slurry for digesting is injected into the digester at locations extending across the horizontal width at one end, parallel to a zone of floating solids in a concentration of solid material between ten and twelve percent, with a momentum of at least 0.1 pound-foot per second. Liquid is taken out of the digester across a trough extending across the width of the digester. Bubbles are broken above the liquid level of the digester by a sieve or surfactant or combination of the two.

13 Claims, 5 Drawing Figures

ANAEROBIC DIGESTER

BACKGROUND OF THE INVENTION

This invention relates to anaerobic digesters.

In a known type of anaerobic digester, the material to be digested is injected at an inlet port or inlet ports and flows to an outlet port, with a residence time between the inlet and outlet of between four days and three weeks while gas is removed from the top of the digester. In a prior art type of this class of anaerobic digester, the material is injected near the center of the fluid at a temperature cooler than the temperature within the digester and removed through another pipe at the outlet.

The prior art digesters of this type have a disadvantage in that the newly entering material tends to fall to the bottom and then rise as it is warmed, causing an increase in sludge at the surface and under some circumstances a flow back toward the inlet of some sludge at the surface.

Certain of the prior art digesters are concrete structures, recessed into the ground as prefabricated units or constructed on site. Such structures have the disadvantage of being too expensive for relatively small digesters. It has been proposed that plastic tubing be used, but the use of such tubing has the disadvantage of making it difficult to gain access to the flow path for maintenance or observation.

SUMMARY OF THE INVENTION

Accordingly, it is an object of the invention to provide a novel digester.

It is a further object of the invention to provide a novel method of operating an anaerobic digester.

It is a still further object of the invention to provide a novel method of fabricating an anaerobic digester.

It is a still further object of the invention to provide a digester in which the new material to be digested is injected in a manner that reduces sludge accumulation in layers at the top or the bottom of the digester.

It is a still further object of the invention to provide a novel anaerobic digester and a method of operating it which reduces sludge accumulation.

It is a still further object of the invention to provide a novel anaerobic digester and method of operating it which provides more efficient flow of gas from the digester.

It is a still further object of the invention to provide an anaerobic digester which incorporates a method of removing bubbles from the surface of the digester.

In accordance with the above and further objects of the invention, an anaerobic digester receives new material to be digested at inlet ports extending in a horizontal line across the digester at a level where the solids accumulate. The new material is injected with sufficient momentum to push the new material within the solid layer toward the outlet and reduce the accumulation of sludge by causing mixing.

The material entering the digester has a normal solid content of between eight and fifteen percent by weight and in the preferred embodiment the solid content is between ten and twelve percent. The material being digested flows with bulk flow from one end of the digester to the other during a residence time that extends between a minimum washout time and approximately three weeks and is removed from the exit port by an opening extending across the transverse width of the digester. The washout time differs from digester to digester and feedstock to feedstock but is always less than four days.

To reduce the accumulation of bubbles, either a surfactant is used or a porous covering, spaced above the surface of the material being digested, to burst bubbles and thus permit ready escape of gas.

To fabricate a relatively inexpensive small-sized digester vessel, tubular members are cut in half and half of the tubular members are laid in a trench end to end with open sides up to form a channel. The walls of the tube must be strong enough to support the slurry and made of a material not susceptible to excessive damage from the environment. The ends of the channel formed by the half-tubes are closed by conforming disc segments, with the inlet disc segment having holes to receive plumbing and the outlet disc segment being cut to form an outlet slot for the effluent. In this manner, a relatively inexpensive digester vessel is made of preformed, commercially standard parts even though the number of such small digesters is relatively small for custom-made wall parts. Although inexpensive, the support is strong, provides access to the flow path, permits bulk flow, and may be quickly constructed.

To prepare a gas bag, a membrane resistant to the material being digested is anchored at one end of the side edge of the tube and laid across the inner surface of the tube to provide a surface against which the material being digested flows. The membrane is anchored along the other side and a means is provided for loosely pulling the membrane over the top of the digester, fastening it along both sides of the tube, to form an elongated gas bag. The two ends of the gas bag are closed.

To control the temperature and provide mixing, pipes enter the digester along the axis and extend along its longitudinal axis. Heated fluid flows through them along the longitudinal axis and thus causes mixing by convection and maintains the digester within the temperature range of between 60 degrees and 180 degrees with 95 degrees Fahrenheit being typical for mesophilic operation. Under some circumstances, thermophilic operation at higher temperatures or psychrophilic operation at lower temperatures may be desirable.

New feedstock materials to be digested are inserted through a horizontal slot or row of orifices at a first end of the digester with a momentum of at least 0.1 pound-foot per second and with a solid content of between ten and fifteen percent. Fluid is removed from the opposite end of the digester in a trough across substantially the entire width of the digester. A porous member or other mechanism is positioned near the top edges of the half-tube to burst bubbles.

As can be understood from the above description, the anaerobic digester of this invention has several advantages such as: (1) it retards the formation of scum by injecting new slurry at the solids zone; (2) it provides an easy method of maintaining a clear, even flow path for the slurry; (3) it permits continued plug flow without the excessive accumulation of solids at the exit end; and (4) in one embodiment, a relatively low-scale, inexpensive digester is formed.

SUMMARY OF THE DRAWINGS

The above-noted and other features of the invention will be better understood from the following detailed description when considered with reference to the accompanying drawings in which.

SPECIFIC DESCRIPTION

Figure 1:
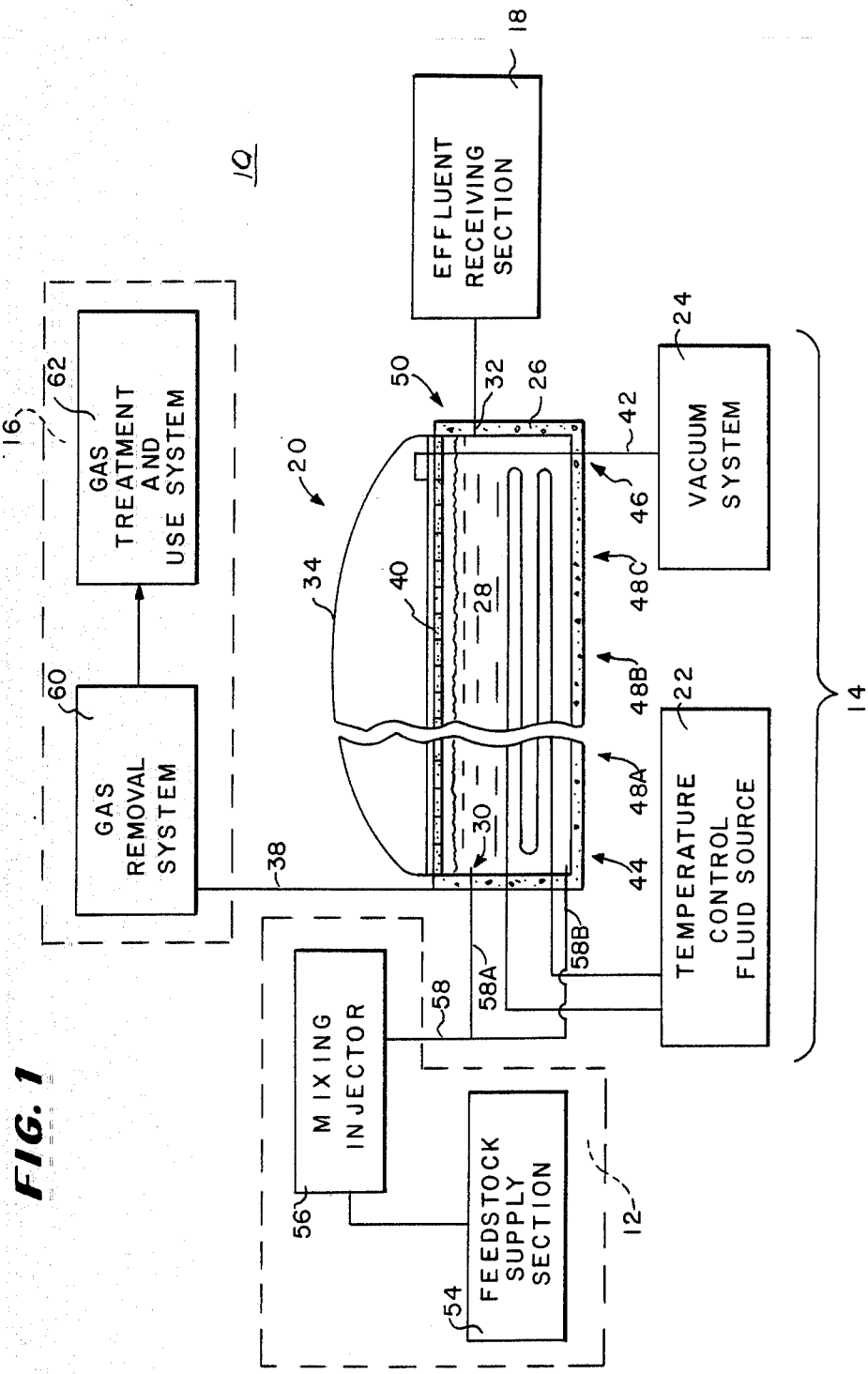
FIG. 1 is a schematic view of an anaerobic digester system incorporating an embodiment of the invention.

In FIG. 1, there is shown an anaerobic digester system 10 having as its principal parts a feedstock supply system 12, a digester section 14, a gas handling section 16 and an effluent receiving section 18.

To process the feedstock, the feedstock supply system 12 communicates with one end of the digester section 14 to supply feedstock to it and the effluent receiving section 18 is connected to the other end to receive the processed feedstock. The gas handling section 16 communicates with the digester section 14 and removes gas formed by the anaerobic digestion of the feedstock which is flowing through the digester section 14.

This digester is of the general type of anaerobic digester disclosed in the U.S. Pat. No. 4,274,838 issued June 23, 1981, to Eugene M. Dale et al., and the disclosure of that patent is incorporated herein. This type of anaerobic digester permits bulk flow of a slurry at a controlled temperature with mild mixing of the slurry within the digester to release gas which is removed from the digester for use.

The digester section 14 includes a digester 20, a temperature control fluid source 22 and a vacuum system 24. The temperature control fluid source 22 supplies fluid to the digester 20 to aid in controlling its temperature and the vacuum system 24 applies a vacuum to remove certain accumulated solids from the bottom to maintain a constant fluid flow rate through the digester 20.

The digester 20 includes an outer wall 26 forming a digester vessel 28 through which the waste material being digested flows from an inlet end 30 to outlet end 32. The digester vessel is closed at the top by a flexible membrane 34 to seal it from the atmosphere and thus provide anaerobic conditions for the production of methane and carbon dioxide from the digestion of the nutrients flowing through the digester.

The cross section of the digester, which is a section through the digester orthogonal to the direction of flow of the material being digested between the inlet 30 and the outlet 32, must be sufficiently large in area to permit bulk flow and is advantageously one fourth to one fifth the axial length, which is the length of the digester in the direction of the flow of waste material. The walls are designed to reduce turbulence and are flat.

Within the digester 20 are a bacterial environmental control system and a gas escape control system. The gas escape control system includes: (1) a conduit system 38 connecting the digester 20 to the gas handling system 16 and providing communication therebetween; and (2) a bubble control system which may include the use of a surfactant to change surface tension or mechanical bubble device such as that shown schematically at 40 or both.

The bacterial environmental control system includes a temperature control system and a flow control system. The temperature control system comprises a plurality of conduits 36 which provide heat to the system and insulation which aids in controlling the temperature for the benefit of bacterial growth.

The flow control system comprises a vacuum system 24 which communicates along the axial length at the sides of the digester wall 26 with the bottom of the digester through a plurality of vacuum conduits indicated generally at 42. This system is intended to remove deposits from the bottom of the digester before they harden and thus maintain a constant cross-section flow path and an absence of abutments which cause turbulence. The coils 36 also cause circulation and mixing of the slurry in a transverse direction.

With this structure, the slurry within the interior of the digester includes vertical zones which are an inlet zone 44, an outlet zone 46 and a plurality of vertical zones in between the inlet and outlet zones, illustrated at 48A, 48B and 48C. Between the inlet and the outlet, different microbe populations grow, each predominantly digesting different material, and the zones are considered the portion of the slurry on either side of the high-density midpoints of each population of different microbes.

For example, near the inlet of a digester, there is a predominance of microbes which break up polysaccharides into simple sugars. Further along the axial length there are zones having a predominance of microbes that reduce the simple sugars to organic acids and still further there are microbes which digest the organic acids.

More specifically, the digester converts complex organic materials such as cellulose, starch, fats and the like into simple organic materials such as sugars, fatty acids and the like near its inlet. Bacteria which thrive on the complex organic materials form one or more zones near the inlet of the digester, and as the slurry moves along the digester, converts the complex organic materials to the simple organic materials. As the simple organic materials are created, more and more bacteria of the type which utilize simple organic materials grow in the slurry and fewer and fewer of the bacterial types that utilize complex materials grow.

In other zones, the simple organic materials such as the sugars, fatty acids and the like are converted by the bacteria to simple organic acids and alcohols. Zones are formed which include predominantly bacteria that utilize the simple organic materials but, as these materials are converted to simple organic acids and alcohols, more and more of the bacteria which utilize the simple organic acids and alcohols grow in the slurry. Thus, as the slurry moves down the digester, still different zones are formed, with bacteria that convert simple organic acids and alcohols to methane and carbon dioxide being predominant.

Turbulent flow that causes mixing between the zones is undesirable because it is undesirable to mix the bacteria from zones under some circumstances. It is undesirable to mix a first bacterial colony of a first zone which contains predominantly bacteria that efficiently digest a first type of material with a second bacterial colony which contains predominantly bacteria that efficiently digest a second type of material but not the first type, since such mixing interferes with the efficient operation of the digester. Thus, it is undesirable to have axial mixing to such an extent as to mix more than twenty percent of one microbial colony which digests one type of material into an area of a concentration of another microbial colony digesting most efficiently another material.

While discrete zones have been described, the zones are not discrete in practice. Instead, the inlet zone 44 is a zone of turbulence with axial mixing of solid particles within the water background. The remainder of the zones, starting with zone 48A through to the exit zone 46 adjacent to the outlet 32, have mixing which is not substantially axial but is transverse roughly in the planes of the cross-sections. This mixing is sufficient to continually mix the microbes with the nutrients which they digest and thus provide an even mixture without having substantial axial mixing. Substantial axial mixing within this specification means mixing which brings more than twenty percent of the microbes digesting efficiently one material into a mixture of a different microbial population which efficiently digests a different material.

The zones are believed to be caused by a combination of movement of the microbes and the efficient reproduction and growth of microbes in the zone which is best suited for them. This occurs as a given sample of the material to be digested moves axially along the digester and remains in the digester for a period of time, called a residence time, selected to achieve the digestion of a predetermined percentage of the solid material in that sample which is typically 20 percent to 60 percent by weight of the solid material.

The residence time for the sample of the solid material for many common waste products such as manure is from four days to three weeks. The length of the digester is selected to provide the proper residence time for a given volume of material at a length to width ratio that avoids excessive mixing between zones at a selected rate of flow. The combination of the rate of flow, length of digester and residence time affects the axial length of each zone of microbes. Each zone has its own length which is different than the axial length of other zones. The minimum residence time is reached when microbes are removed with the effluent in such quantities as to terminate digestion or reduce it below an effective rate. This is called washout time.

The actual dimensions of a digester are an economic consideration and are determined by calculating the cost efficiency. The cost efficiency is affected by the type and location of the material at hand for digesting, the size and configuration of the digester and the use of the gas and undigested product of the digester. Each digester must provide bulk flow and digest a sufficient amount of the solids for economic handling. The undigested product of the digester may be used as bedding for livestock, fertilizer and livestock feed.

In addition to axially positioned vertical zones of predominantly different microbes, the digester has layers or horizontal zones of density in elevation. The material within the digester vessel 28 is a suspension of solid material in liquids and generally contains fifteen percent or less of solid material by weight, the rest being water. More commonly it is approximately ninety percent water and ten percent solid material by weight.

The solid material has different densities and, if it is lighter than water, forms a horizontal zone at the top of the digester, such as that indicated at 50, extending both axially and transversely to form a layer near the top but, if heavier than water, forms a layer at the bottom, such as shown at 52. In the case of a common material such as many manures, more than 75 percent by weight of the insoluble solid material is less dense than water and forms a layer at the top.

In this specification, if sixty percent or more of the organic insoluble material ordinarily used in a digester is lighter than water, the digester will be considered a top-zone digester and, if sixty percent or more is heavier, it will be considered a bottom-zone digester.

The temperature control system utilizes mean for adding heat and means for controlling the loss of heat. For best results, the heat is added from a temperature control fluid source 22 through the conduits 36 which extend along the axial length of the digester. The fluid may be heated water and is less than 160 degrees Fahrenheit but greater than 60 degrees Fahrenheit. It controls the temperature of the liquid to that most suitable for bacteria, which, in the usual mesophilic or thermophilic cases, is not less than 95 degrees Fahrenheit. It also creates convection currents which cause transverse mixing sufficient to spread the bacteria among the nutrients without causing substantial axial mixing.

The gas escape control system includes: (1) a pressure control system, to be described hereinafter, for maintaining the pressure within the bag 34 within limits; (2) conduits to supply gas to the gas handling system 16; and (3) bubble control devices. One suitable bubble control device is a coarse fibrous material, such as rigid open-celled foam, which permits the gas to escape through the foam while breaking bubbles on its surface, positioned slightly above the surface of the liquid To supply material to the digester vessel 28 for digestion and conversion to gas, the feedstock supply system 12 includes a feedstock supply section 54 and a mixing injector 56 connected together to supply the feedstock to the digester vessel 28. The feedstock supply section 54 receives a material such as, for example, animal waste or dairy waste. Commonly it may be manure, whey, packing house waste, food processing waste or the like. It is formed into a slurry in a sump within the feedstock supply section 54 in a manner known in the art and conveyed to the mixing injector 56 by a conveyor system or a system of open conduits or closed conduits or the like.

The mixing injector 56 includes conduits indicated schematically at 58A and 58B which may be connected to point directly into an upper zone 50 or a lower zone 52. They may be a series of conduits opening into the digester to which the slurry may be pumped to enter at an upper zone or a lower zone depending on the waste material for which the digester is designed.

The injected material enters the digester vessel 28 at a relatively high momentum to cause turbulence and thus mix the particles at the entrance and at the same time move the solid material toward the outlet end of the digester along its axis. Thus, the mixing injector is positioned in accordance with the floating zones of solid material to create mixing turbulence at the entrance and thus retard scum formation.

The injector injects new slurry predominantly adjacent to the zone of maximum solid material with sufficient momentum to move inwardly into the solid material. It is injected at a pipe velocity sufficient to provide momentum that mixes the solid materials. This momentum must create a force on the solid particles sufficient to overcome the forces of adhesion between solid materials and thus to reduce the tendency for agglomeration of solid particles.

The momentum for each gallon of slurry is determined in each case depending on the adhesive forces of the particles within the slurry but is greater than 0.1 pound-foot per second. It must be sufficiently great to have a momentum substantially greater than the forces, such as inertial forces and adhesion forces, of the cross-section of the solid zone against which it impacts for a distance of several inches. It must be sufficiently greater than that group of forces to move the particles upwardly, downwardly and in transverse direction and thus to scatter them.

The gas removal section 16 includes a gas removal system 60 and a gas treatment and use section 62. The gas removal system 60 communicates with the flexible membrane 34 to receive gas upwardly. An escape vent, to be described hereinafter, controls pressure for safety reasons and the gas is accumulated in the removal system and transmitted to the gas treatment and use system 62.

The gas is substantially a mixture of methane gas and carbon dioxide and may be used by an internal combustion engine or other type of combustion engine or may be burned to supply heat for a boiler or the like. It may also be used to supply gas for a boiler to heat water within the temperature control fluid source 22 for application through the conduits 36. The internal combustion engine or other engine may be used to generate electricity.

The effluent receiving section 18 receives the digested fluid and transmits it for further treatment or use or recirculation. It is essentially a trough so as to receive fluid across the entire width of the digester, thus permitting a smooth flow of fluid without turbulence near the end and without the accumulation of solid material in corners or the like.

Figure 2:
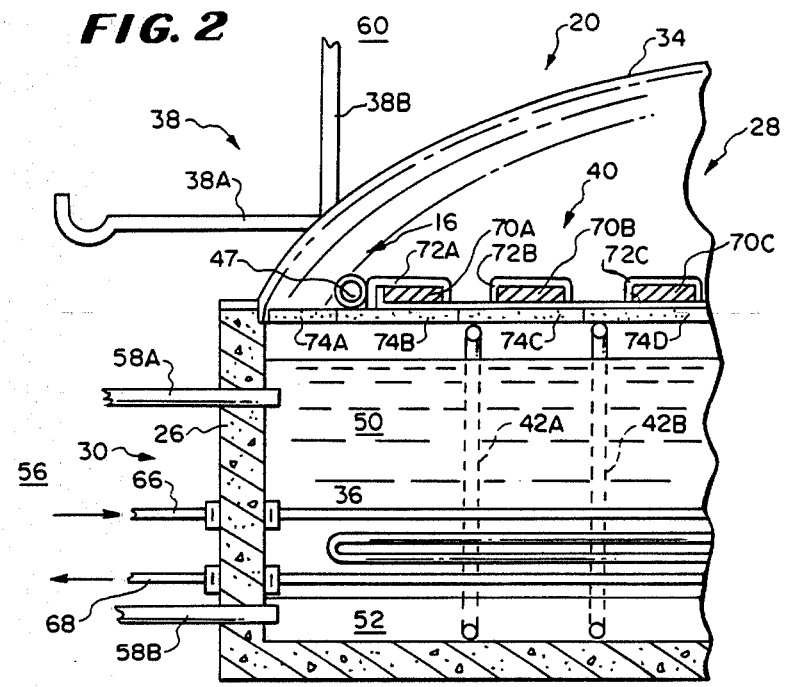
FIG. 2 is a fragmentary sectional view of a portion of the digester of FIG. 1.

In FIG. 2, there is shown a fragmentary sectional view along the longitudinal axis in elevation showing the inlet section 30 of the digester 20 and the mixing injector 56, having the alternative inlet pipes 58A and 58B, the mechanical bubble suppressor 40, the portion 38 the gas removal system 60 which communicates with the interior of the gas bag 34, the piping system 36 which forms part of the temperature control system and two vacuum conduits 42A and 42B which are shown by way of example to illustrate the operation of the vacuum system 24 (FIG. 1).

Although both of the alternative constructions of the inlets for the mixing injectors 58A and 58B are shown in FIG. 2 for either a top zone or a bottom zone, in practice there is only one. Usually the digester is constructed for a particular type of waste material and it is known in advance if the waste material will be buoyant or not. Thus only one of the inlet pipes 58A and 58B needs to be employed. In either event, the one is selected which provides sufficient momentum of solid particles into the solid zone to intersperse the new colder particles with the warmer particles which have collected in the zone.

The mixing injector 56 should: (1) have its injection portion 58A for a top zone positioned at a location centered on the solid zone 50 within the digester vessel 28 to provide a maximum mixing; and (2) inject the new slurry at a temperature colder than that within the vessel 28 across as much of the cross-section as possible with sufficient momentum to thoroughly mix the particles. This momentum is sufficient to: (1) separate some particles which have agglomerated within the layer; and (2) create circulation by forward momentum. The differences in temperature between the injected slurry and the layer of scum within the digester also cause some circulation.

It is desirable to avoid injecting the new slurry beneath the top zone and close to it. Under some circumstances, it flows beneath the zone and causes the zone to move back toward the inlet and be compacted further. Moreover, when injected underneath the zone, the particles rise as they warm and add to the scum on the surface.

When the outlet portion of 58B of the mixing injector 56 is utilized, the momentum must be sufficient to inject the particles across a cross-section just as in the top zone 50. It is preferred that the material being injected is warmer than the scum in zone 52A to cause upward mixing but some beneficial results are obtained even if it is colder.

In the preferred embodiment with a top zone, the inlet portion 58A is located approximately sixteen inches from the top of the sides of the vessel 28 and approximately eight inches below the liquid. As illustrated in FIG. 2, the inlets 58A are below the top of the sides of the digester wall 64 and are immersed in the liquid within the digester 28 centered on a layer 50 which normally extends from the surface to a depth approximately eight inches below the top of the surface of the slurry though it may rise and fall and may differ in depth from situation to situation. The fluid is injected at approximately two feet per second through inlet pipes having an internal diameter of three inches.

To cause circulation and temperature control, the pipes 36 are three-inch pipes which enter the wall 26 of the digester 20 at two points 62 and 64 and extend longitudinally along the central axis of the digester for the larger portion of its length. Several loops may be formed to maintain the temperature at approximately 95 degrees. The heated fluid enters one of the pipes such as at 62 and exits at the other such as at 64 and flows along the central axis to add heat. The pipes 36 are located in a vertical plane below the surface of the liquid in a line from near the surface to the bottom. They are spaced to insure that cold layers near the bottom are heated and to encourage circulation.

The heat added and the insulation outside the digester should be such as to maintain temperature relatively constant and cause mild transverse circulation within the digester to an extent that maintains a small range of temperature difference from the central axis to the outer wall of the digester. In the preferred embodiment, a two-degree difference in gradient from the center to the side of the digester is maintained and is sufficient to sustain stirring.

The temperature should be varied only very slowly in time and distance. A two-degree Fahrenheit variance per week is typical and it should be less than fifteen degrees Fahrenheit per week. There should not be more than a five-degree Fahrenheit difference between the center and the outer wall of the digester. Moreover, the temperature gradient along the axial length can only be mild and changed slowly. Four degrees for each hundred feet of length is typical and a difference should be less than fifteen degrees Fahrenheit for each hundred feet of length.

While the temperature control equipment can take many forms and still perform its functions, the hot-water pipes 36 should extend from a lower point which is in the range of touching the bottom and three feet from the bottom to a higher point which is one foot to three feet below the surface. In the present embodiment 36 includes ten two-inch-diameter pipes, one over the other, evenly spaced to provide substantially uniform heating along a vertical plane at the center of the digester.

The bubble-bursting system 40 includes a plurality of steel cross-beams extending transversely across the digester and resting on the top of the walls 64 such as those shown at 70A through 70C. These steel cross-beams extend across the entire axial length of the digester 20 on four-foot centers. Beneath the beams and held by ropes such as those indicated at 72A-72C are a plurality of porous styrofoam panels such as those shown at 74A-74C.

The panels rest side by side and are eight feet long so as to extend across the space between any two cross-beams and partly into the barrier between the next two cross-beams on either side. They are tied by the ropes such as those shown at 72A-72C to maintain them in position side by side to form a continuous cover spaced above the liquid level within the digester. As gas escapes from the digester, it forms bubbles which inhibit the escape of gas through the gas escape system 60. However, when the bubbles reach the styrofoam, they burst and the gas passes through the styrofoam, principally passing between panels.

The panels also prevent excessive heat loss through the top surface and gas bag. The thickness of the panels is designed to preserve heat under the colder temperatures in the location of the digester.

Although styrofoam has been disclosed to prevent an excessive accumulation of bubbles within the gas bag of the digester, obviously other methods may be used to burst the bubbles. Moreover, materials other than styrofoam may be used, for example, to burst bubbles or a surfactant may be used to reduce the surface tension of the liquid within the digester and thus prevent bubble formation.

To prevent a build-up of material at the bottom of the digester, a plurality of vacuum tubes extend above the surface along the walls 26 down to the bottom of the digester. They may be outside the walls or inside the walls until they near the bottom, at which point they must have an opening inside the digester. Two such tubes are shown at 42A and 42B with the tubes passing outside the walls 26, as shown by hidden lines, and entering at 43A and 43B to communicate with the bottom. While two tubes are shown in FIG. 2, a plurality of tubes are located at spaced-apart points extending across the entire axial length of the walls 26.

The form of the vacuum tube depends on the type of material to be vacuumed from the bottom. Fine particles which are not hardened are removed by agitating the particles so that they form a suspension in the liquid and pulling the particles up by vacuum force with liquid. In this embodiment, the rate of pulling by the vacuum must be sufficiently great to prevent the particles grom settling out as liquid is pulled toward the top. The particles are filtered from the liquid and the liquid recirculated back into the digester.

The second form of vacuum is used when there is a relatively thick scum of particles with high adhesion. This type of vacuum device has a diameter sufficiently small so that the vacuum pressure necessary to pull material from the bottom to the top against the weight of a full column is not greater than the force which ruptures the bed of thick material near the tube to permit more mobile fluid to flow through it.

In the preferred embodiment, vacuum is created through four-inch-diameter pipes that enter the digester along the line 69 where the wall slopes to a point. The pipes are positioned every three feet along the wall and extend to within one foot of the lowermost portion of the sloped bottom where the sludge accumulates.

To remove gas from the digester, the gas removal system 60 includes an inlet communicating with the interior of the gas bag 34 above the level of the fluid within the digester such as that shown at 76. Two conduits 38A and 38B communicate with the outlet 76, the conduit 38B being a safety conduit for releasing gas when the pressure within the bag 34 exceeds a predetermined limit which is considered dangerous. That limit may be established by the amount of pressure that causes fluid to be forced outside of wall 26 or tears the bag 34 or does any other damage.

To prevent the pressure from exceeding the permissible limits, a pressure-release means is included in the system such as a trap containing an appropriate head of water or any other pressure-release mechanisms such as a spring-biased release valve. The outlet of the pressure-release means should be covered with a flame-retarding screen known in the art at the point where it may release gas to the atmosphere when the pressure is exceeded. The gas removal conduit 38A extends outwardly between the outlet 76 and the pressure release conduit 38B. It preferably contains a trap to remove moisture condensing in it and leads to the gas treatment and use system 62 described in connection with FIG. 1.

Figure 3:
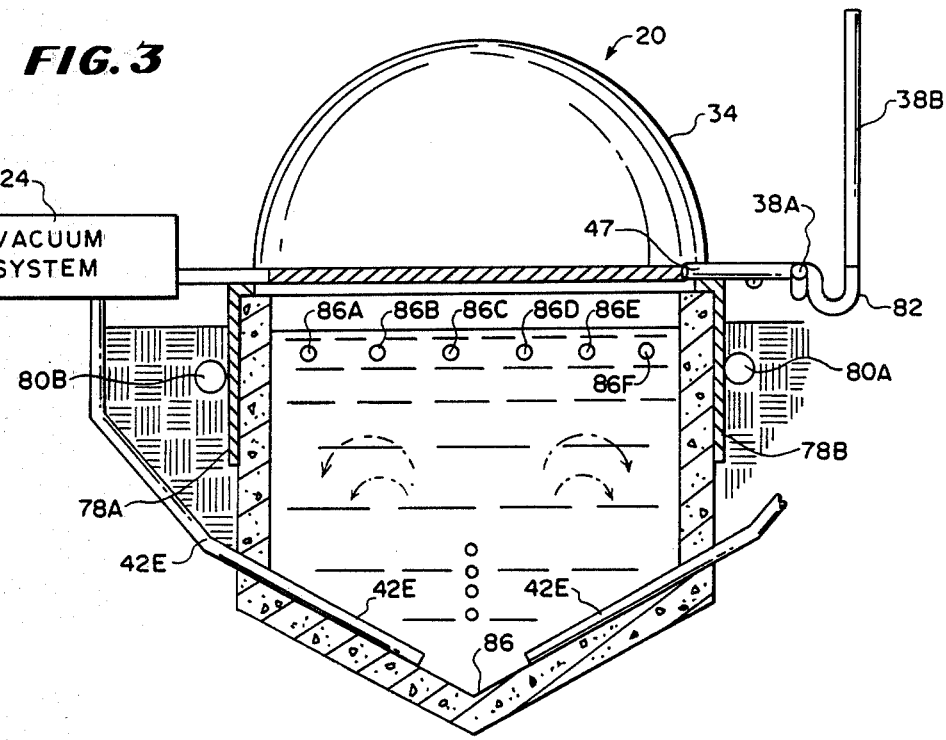
FIG. 3 is a transverse sectional view of a portion of the digester of FIG. 1.

In FIG. 3, there is shown a transverse sectional view facing the inlet 30 of the front end of the digester 20 and having portions of the temperature control pipes 36, the outlets from the injector conduits 58A, the bubble-bursting mechanism 40, the vacuum system and the gas removal system 28.

As shown in FIG. 3, the conduits 36 cooperate with insulation on the outside of the walls 26 such as that shown at 78A and 78B. Normally the digester vessel is at least partly within the ground to provide still further insulation. Moreover, while it is not usual, it is possible to provide heating pipes such as those shown at 80A and 80B to receive a heated fluid or a coolant fluid for additional heat outside the walls. The conduits 36 may contain cooling fluid as well as the conduits 80.

In the preferred embodiment, the pipes 36 are two-inch-diameter pipes and water flows through them at approximately 150 degrees Fahrenheit. Of course, for operation of the digester in the thermophilic range, the temperature of the water will be higher and will be lower for operation in the mesophilic or the psychrophilic range. The temperature differential from the pipes 36 to the walls 26 on the inside is approximately two degrees Fahrenheit and this temperature is maintained in spite of a lower temperature of the earth by transverse circulation of the liquid in the digester vessel as indicated by the arrows.

At temperatures below 65 degrees Fahrenheit, there is very little bacterial action under most circumstances. At temperatures between 65 degrees and 90 degrees Fahrenheit, usually acid-forming bacteria work faster than acid-consuming bacteria and the digester may go sour. Thus, usually the temperature is maintained above 90 degrees Fahrenheit.

This circulation is normally upwardly and outwardly toward the walls from the conduits 36 with cooling taking place against the walls and sinking. This slow circulation in a transverse direction mixes the slurry to: (1) expose it better to bacteria; (2) prevent the formation of a thick floating zone or bottom zone of sludge; and (3) maintain a substantially uniform transverse-direction temperature gradient of less than fifteen degrees Fahrenheit for each hundred feet through the slurry.

The insulation and/or the combination of the pipes 36 and 80 containing cooling or heating fluid maintain the temperature within the digester vessel at the desired temperature which is normally between 60 degrees and 160 degrees Fahrenheit. Variations in temperature with time are only made slowly, such as two degrees Fahrenheit per week, to permit the microbes to adjust to the changes. The variation between the slurry inside the digester and the earth outside the digester is usually sufficient to cause circulation and preferably should be in the order of at least forty to fifty degrees Fahrenheit.

As best shown in FIGS. 2 and 3, the conduits to the gas handling section form a manometer at 82 to maintain pressure which permits the venting of gas from within the gas holding membrane 34 if it should become excessive. The pressure can be set by the amount of liquid in the manometer 82 in a manner known in the art. The conduit 38A is used to remove gas for the gas handling system 60 (FIG. 1), which may be a compressor or dryer or other gas-treatment facility, and includes a convenient trap at 84 for draining fluids when necessary.

By using an insulator such as the styrofoam panels, the gas holding membrane 34 can be kept cool. This reduces the humidity of the gas because of the condensation of water on the gas holding membrane and thus reduces condensation of water in the gas line and corrosion from hydrogen sulfide. Thus, the insulators are selected to have a material and thickness that reduces heat escape while maintaining sufficient porosity to permit the escape of gas.

The vacuum system 24 is connected to a plurality of vacuum conduits, one being shown at 42E, designed to extent to the bottom centerline of the digester at 86 where the sloping walls meet at the lowest line along the longitudinal axis, as an illustration of one embodiment. As described above, a number of different embodiments may be used, including one to: (1) agitate the aaterial in the digester by a downward flow of water to create a suspension; and (2) pull the liquid with the suspended particles upwardly. Another embodiment is able to draw sludge upwardly without opening pathways for less dense liquids. These conduits are narrow and use less pressure by controlling the size of the conduit. The vacuum may also be applied gradually to preserve a low pressure at the inlet port.

The foremost part of the bubble-bursting configuration is shown in FIG. 3 with the first steel cross-bar 70A supporting the first styrofoam panel 74A. Of course, there are a plurality of parallel steel cross-plates 70A extending the axial length of the digester vessel and resting on the tops of the walls 26, which support a continuous sheet of bubble-bursting material such as the styrofoam panels spaced at a distance from the highest level of slurry within the digester vessel.

The injector conduits 50A are shown having a plurality of outlets 86A-86F spaced approximately six feet, center to center, across the transverse length of the digester. The injector conduits are spaced to provide a relatively uniform flow of slurry into the digester parallel to the zone of sludge that is formed.

In the embodiment of FIG. 3, the solid zone is a top zone and the injector conduits face the zone and inject slurry at a temperature slightly colder than the solid sludge at that level. The slurry has sufficient momentum to separate particles of the digester slurry which have been held together by adhesion. Thus the new slurry mixes with the particles prior to being warmed and creates turbulence as it tends to sink because it is colder and then tends to rise as it is heated by the surrounding liquid. This turbulence tends to prevent the accumulation of a solid sludge layer at the top of the digester.

Figure 4:
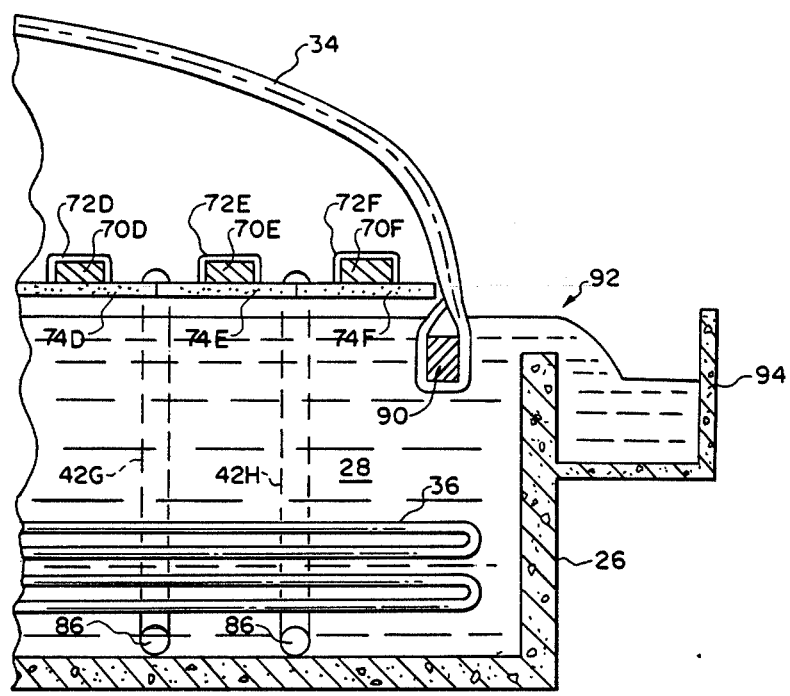
FIG. 4 is another fragmentary sectional view of a portion of the digester of FIG. 1.

In FIG. 4, there is shown a fragmentary sectional view along the longitudinal axis of the digester 20 and the effluent receiving section 18 having an outlet slot 92 for the flow of fluid from the digester vessel 28 to the effluent receiving section 16 over a portion of the walls 26. As shown in this figure, the membrane 34 is mounted to a beam 90 which extends between the walls 26 in a transverse direction from wall to wall submerged within the liquid of the digester vessel 28 and spaced a short distance from wall 26 at the outlet end 32 of the digester.

The membrane 34 is wrapped around the beam 90 and extends upwardly to the top of the wall 26 to provide a seal, leaving the opening 92 between the wall 26 at the exit end 32 and the membrane 34, through which opening the effluent flows. The wall 26 is shorter at this point and is cut downwardly approximately six inches lower than the wall top at other places around the digester vessel 28 to permit the flow across the entire transverse section of the digester into the effluent receiving section 18.

To receive the effluent, the receiving section 18 is a trough having walls 94 to convey the fluid to a pond or other convenient location. With this structure, the fluid flows in a streamlined manner without excessive transverse turbulence across the entire transverse distance of the digester over the shortened wall portion at 32 into the effluent receiving section 18. Because of this flow across the entire section, scum does not accumulate to any extent against the sides of the outlet and the flow is relatively continuous and streamlined.

Figure 5:
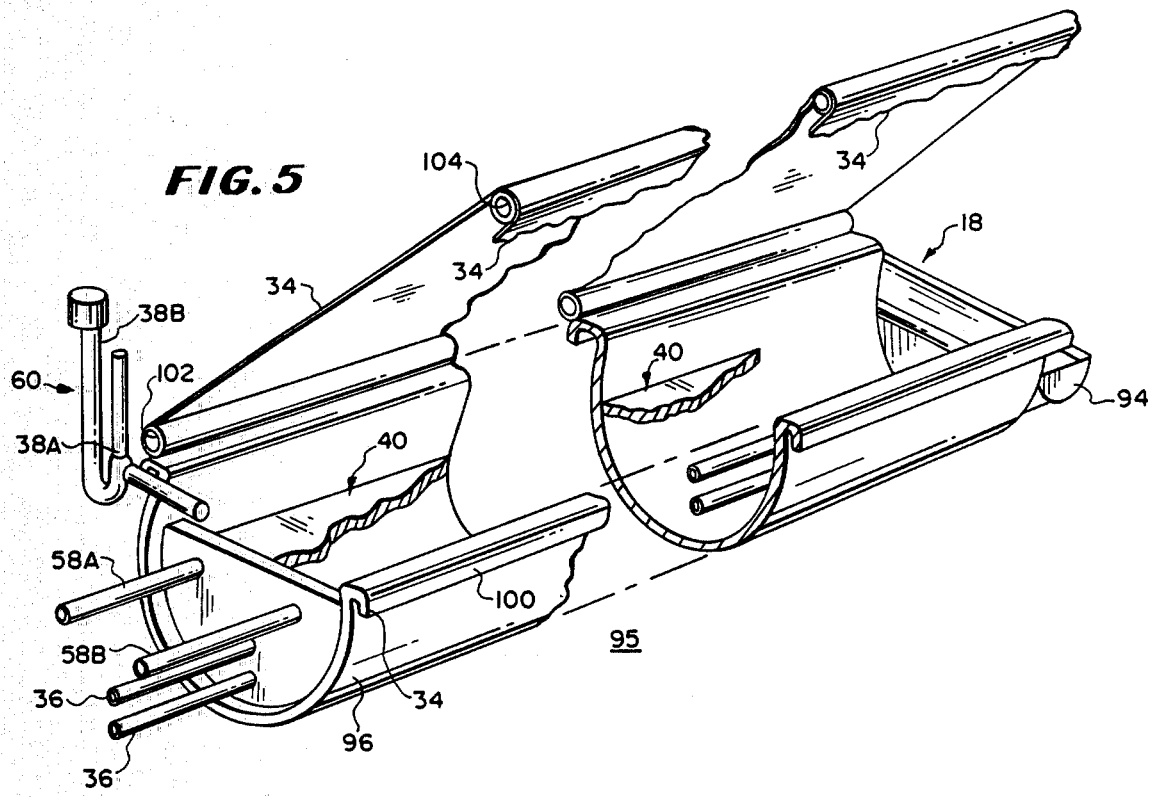
FIG. 5 is a simplified perspective view of another embodiment of the digester.

In FIG. 5, there is shown a simplified perspective view of another embodiment of digester 95. The digester 95 has many parts which are similar to the digester 20 (FIGS. 1–4) except that the digester 95 is intended to be of smaller scale than the digester 20. The similar parts such as the membrane 34, the gas handling system 60 with the conduits 38A and 38B, the injector 58A, the heating pipes 36 and the bubble-bursting means 40 are all substantially the same except they may be smaller.

The digester 95 includes a channel wall 96 with a membrane 34 extending over one edge such as that at 100 and lying along the inner surface of the channel wall 96 to its opposite side. At its opposite side it is anchored downwardly by an axially extending member 102. The membrane 34 extends loosely over the top and at its opposite end is anchored a second elongated member 104 so that the digester may be opened by pulling the member 104 to the same side as the member 102 and may be closed to form a gas bag by pulling it over the open end of the channel wall 96 and resting it on the opposite side.

The channel wall 96 forms a liner for a trough and may be formed of half of a cylindrical tube of sufficiently strong and environmentally stable material such as plastic, concrete or steel. It opens upwardly in a trench forming a channel to accommodate a relatively low rate of flow of material to be digested. While a cylindrical tube is disclosed any tubular shape can be used and sections may be located side by side.

In constructing the digesters 20 (FIGS. 1-4) or 95 (FIG. 5), a foundation is prepared by excavating a channel or trough within the earth. For the digester 20, the walls are usually formed of concrete and are a permanent structure. For the digester 95, a tube is normally halved and the half inserted in a trench opening upwardly.

The injection pipes 36 are mounted extending along the longitudinal axis of the digester and a mixing tank or sump is prepared on the inlet end. The pipes 36 are connected to a source of heated fluid, which is heated by any suitable means such as by a boiler provided on site for that purpose. The closed entrance end is poured concrete in the embodiment of FIGS. 1-4 and may be a half cylindrical member of plastic, steel or wood in the embodiment of FIG. 5.

A plurality of holes are located to receive the ejector conduits 58 so that the ejector conduits 58 extend horizontally in a transverse direction at the level of the solid layer in the slurry. In the embodiment of FIG. 5, this position is beneath the maximum diameter of the half-tube and near the top of that diameter is a bubble-bursting screen which may be mounted from edge to edge.

Prior to inserting the tubes in the embodiment of FIG. 5, a membrane is staked to the forward side by wrapping it around an elongated beam of wood or pipe 100 and that pipe is anchored to the ground or to other suitable support. The membrane is then laid over the inner surface of the tube wall 96 to provide a bottom sealing surface for the slurry. Several tubes of the same size may be cut in half and laid end to end for one elongated digester to provide an adequate residence time of between one week and three weeks for the slurry.

With the construction of FIG. 5, a relatively economical digester for handling low rates of flow of slurry may be formed from inexpensive tubing with a surface that is protected by the membrane. On the opposite side of the tube, the membrane is mounted to the ground by another elongated member and a length of it is fastened to a third member so that it can be pulled loosely over the tube to form a gas bag. The tube can be easily opened when necessary for cleaning deposits along the bottom or making repairs or the like and may be closed to provide the anaerobic atmosphere necessary for the production of methane.

At the exit ends of the digesters, an effluent receiving mechanism 18 is constructed by building within the ground a trough and by making the wall at the end lower. The gas bag terminates short of the end of the digester so that the effluent may flow out from the bag and over the wall across the entire transverse length of the digester to provide relatively streamlined flow into the trench to remove the waste material.

In the operation of the digesters of FIGS. 1-4 and of FIG. 5, naterial to be digested such as manure or the like is gathered and conveyed to the mixer in which it is pumped and mixed with sufficient water to form a slurry. The slurry is then pumped through the ejectors across the length of the digester at a level in which, during operation, the solids form a zone. For certain types of material such as cow manure, there is a zone in the upper portion of solids because the solids are principally less dense than water. For certain other types of waste material, the zone is at the bottom.

The slurry is injected with sufficient momentum to cause turbulence. It contains solid particles of sufficient amounts to reduce the tendency to settle or float. In the preferred embodiment, the amount of solids by weight is between ten and twelve percent but may fall in other embodiments between eight and fifteen percent. In still other embodiments because of factors such as viscosity of the slurry, the percentages may be different but are selected to provide a low separation factor.

"Separation factor" in this specification means the tendency for solid particles to separate from the slurry as sediment or as a floating sludge in the digester. As the separation factor increases, the tendency for the particles to separate increases.

The separation factor is approximately proportional to the sedimentation constant and has a substantially direct proportionality to the square of the radius of the particles and a substantially direct proportionality to the difference between the specific volume of the particles and of the slurry and a substantially inverse proportionality to the viscosity of the slurry. The separation factor is increased by surfactants under most circumstances.

From the above discussion it can be understood that the separation factor increases as the particle sizes increase, decreases as the amount of particles in the slurry increases, decreases as the viscosity increases and normally increases when a surfactant is added. The bubbling effect also has a tendency to increase the separation factor by carrying particles to the top of the slurry but bubbling is decreased by the surfactant.

The slurry is injected opposite the zone to mix with the solid material and create turbulence near the entrance end of the digester. The slurry moves slowly within the anaerobic atmosphere for a residence time of between one week and three weeks while methane gas is produced by the bacteria and collected for use. As the slurry moves along the axial length, it is heated by central pipes to keep it within the desired temperature and to cause circulation which is transverse to the tube.

Bubbles which rise from the surface and tend to impede gas collecting are squeezed against a porous member, causing them to burst. The bubble-bursting member is above the surface of the liquid so as to not impede the movement of scum that may form on the top of the liquid during movement. At the exit end, the slurry flows beneath the edge of the gas holding membrane and over a lower portion across the entire length and has streamline flow which tends to carry with it solid material so that the solid material does not accumulate.

During operation, deposits on the bottom are pulled out by vacuum through a plurality of vacuum conduits. The vacuum conduits create a suspension at the bottom by ejecting fluid downwardly to stir it up or stirring by other mechanism and pulling the bottom deposits upwardly, at which point they are filtered and the liquid returned. In another embodiment, to accommodate muck at the bottom, a vacuum is used which has a sufficiently narrow inner diameter to prevent the water from forcing its way through the muck and instead to cause solid plugs of the muck to be pulled up through the vacuum.

As can be understood from the above description, the anaerobic digester of this invention has several advantages such as: (1) it retards the formation of scum by injecting new slurry at the solid zone; (2) it provides an easy method of maintaining a clear, even flow path for the slurry; (3) it permits continued plug flow without the excessive accumulation of solids at the exit end; and (4) in one embodiment, a relatively low-scale, inexpensive digester is formed.

Although a preferred embodiment of the invention has been described with some particularity, many modifications and variations of the preferred embodiment are possible without deviating from the invention. Therefore, it is to be understood that, within the scope of the appended claims, the invention may be practiced otherwise than as specifically described.

What is claimed is:

1. Apparatus comprising:

walls forming a digester vessel closed to the atmosphere;

said digester vessel having an inlet side and an outlet side defining between them a flow path in a longitudinal direction along a longitudinal axis along which material to be digested flows and having transverse planes extending in a transverse direction perpendicular to the longitudinal axis;

means for removing gas from said digester vessel;

said digester vessel having dimensions in the transverse planes sufficiently large to permit a bulk flow of a slurry of material to be digested containing between ten and fifteen percent of solids between said inlet side and said outlet side along the flow path and having a horizontal zone containing substantially more of said solids than the remainder of the digester material;

means for causing mixing of said material in said digester vessel in the transverse direction without substantial mixing in the longitudinal direction;

means for injecting new slurry into said digester vessel at said inlet end through a plurality of openings spaced apart in the transverse direction across a transverse line at said inlet end;

the sum of the diameters of said openings being at least two percent of the transverse length in the transverse direction;

said openings being spaced no more than twenty feet apart along the transverse direction;

said transverse line being at the same vertical elevation as said zone so that at least ninety percent of said openings and said zone of solid material overlap, whereby said new material flows into said zone of solid material;

said means for injecting including means for injecting a slurry having between ten and fifteen percent solid material into it with a momentum per cubic foot of inlet slurry of at least 0.1 pound-foot per second, whereby the scum layer boundary within said digester vessel is reduced; and said means for causing mixing in the transverse direction including means for controlling the temperature of said slurry to maintain it between 95 degrees and 140 degrees Fahrenheit.

2. Apparatus according to claim 1 in which said flow path in said longitudinal direction includes a plurality of vertical zones of microbes and said means for causing mixing in said transverse direction includes means for causing transverse mixing without causing sufficient mixing in the longitudinal direction to mix more than twenty percent of one vertical zone of microbes with an adjacent vertical zone.

3. Apparatus according to claim 2 in which said outlet side includes an opening extending for at least 75 percent of the transverse direction between the inner side walls of the digester vessel, whereby said slurry flows out of the digester vessel in relatively streamlined flow.

4. Apparatus according to claim 3 including a vacuum means for removing sludge from the bottom of the digester vessel by vacuun pressure.

5. Apparatus according to claim 4 including means spaced from the top of said slurry for bursting bubbles formed on the surface of said slurry.

6. An anaerobic digester comprising:

a digester vessel having an inlet side and an outlet side with a longitudinal axis extending therebetween and having dimensions in a direction transverse to the longitudinal axis sufficient to permit a bulk flow of slurry between the inlet side and the outlet side;

said anaerobic digester being closed to the atmosphere and having a slurry flowing between the inlet and the outlet sides containing one of an upper and lower horizontal solids zones; and means for injecting new fluid into said horizontal solids zone with sufficient momentum to mix the solid particles of said new fluid with the particles in the solids zone to cause mixing near the inlet side of said vessel, whereby scum accumulation is reduced.

7. A digester according to claim 6 in which said outlet side includes means extending transversely across said digester for causing the fluid from said digester to flow in a streamlined path.

8. An anaerobic digester according to claim 7 in which said means for injecting includes a plurality of inlet pipes spaced from each other in a direction transverse to said longitudinal axis and communicating between the inside of the vessel and a source of new slurry.

9. An anaerobic digester according to claim 8 in which the digester vessel includes:

means for removing gas from said digester;

said digester having a dimension in the direction transverse to said longitudinal axis sufficiently large to permit a bulk flow of a slurry of material to be digested containing between ten and fifteen percent of solids between said inlet side and said outlet side along a flow path along the longitudinal aixs and having a horizontal zone containing substantially more of said solids than the remainder of the digester material;

means for causing mixing of said material in said digester in a transverse direction without substantial mixing in the direction along the longitudinal axis;

means for injecting new slurry into said digester at said inlet end through a plurality of openings spaced apart in the direction transverse to the longitudinal aixs across said inlet side;

the sum of the diameters of said openings being at least two percent of the dimension in the direction transverse to the longitudinal axis;

said means for injecting including means for injecting a slurry having between ten and fifteen percent solid material into it with a momentum per cubic foot of inlet slurry sufficient to reduce the scum layer boundary within said digester vessel; and said means for causing mixing in the direction transverse to the longitudinal axis including means for controlling the temperature of said slurry to maintain it above 60 degrees Fahrenheit.

10. An anaerobic digester according to claim 9 in which:

said flow path along said longitudinal axis includes a plurality of vertical zones of microbes and said means for causing mixing in the direction transverse to the longitudinal axis includes means for causing transverse mixing without causing sufficient mixing in the direction of the longitudinal axis to mix more than twenty percent of one vertical zone of microbes with an adjacent vertical zone; and said means for causing mixing includes means for controlling the temperature to maintain it below 160 degrees Fahrenheit.

11. An anaerobic digester according to claim 6 in which the digester means includes:

temperature control means having a heat source for providing sufficient heat to maintain no more than a fice-degree Fahrenheit difference between the heat source and the external side of the digester with the fluid in the inside of the digester vessel being less than 180 degrees Fahrenheit; and said temperature control means includes insulative material positioned outside of the digester vessel and heat conduits serving as the heat source inside the digester vessel.

12. An anaerobic digester according to claim 11 further including:

an elongated ditch;

said digester vessel including an elongated member having a U-shaped cross section with an open top;

said elongated member being positioned in the ditch with the open top facing upwardly;

said digester vessel further including a flexible membrane extending across the inside of the U-shaped rigid member from one side to the other side and over its top positioned to contain the slurry;

means for anchoring said flexible membrane on both of said one and other sides of the rigid member; and said membrane forming a bag-like top cover over said rigid member to receive gas and seal from the atmosphere.

13. An anaerobic digester according to claim 12 in which the flexible membrane is one integrally formed plastic sheet.

* * * * *